United States Patent
Cawley et al.

(10) Patent No.: US 9,545,275 B2
(45) Date of Patent: *Jan. 17, 2017

(54) MEDICAL DEVICE LOCKING MECHANISMS AND RELATED METHODS AND SYSTEMS

(71) Applicant: US SPINE, INC., Salt Lake City, UT (US)

(72) Inventors: Trace R. Cawley, Austin, TX (US); David Crook, Mineola, TX (US)

(73) Assignee: US SPINE, INC., Salt Lake City, UT (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/277,001

(22) Filed: May 13, 2014

(65) Prior Publication Data

US 2014/0249587 A1 Sep. 4, 2014

Related U.S. Application Data

(63) Continuation-in-part of application No. 11/875,072, filed on Oct. 19, 2007, now Pat. No. 8,721,693, which is a continuation-in-part of application No. 11/804,545, filed on May 18, 2007, now Pat. No. 8,840,650.

(51) Int. Cl.

| *A61B 17/84* | (2006.01) |
| *A61B 17/80* | (2006.01) |
| *A61B 17/70* | (2006.01) |
| *A61B 17/86* | (2006.01) |

(52) U.S. Cl.
CPC ....... *A61B 17/8038* (2013.01); *A61B 17/7059* (2013.01); *A61B 17/8033* (2013.01); *A61B 17/8047* (2013.01); *A61B 17/8052* (2013.01); *A61B 17/8605* (2013.01)

(58) Field of Classification Search
CPC ............ A61B 17/8052; A61B 17/8038; A61B 17/8033; A61B 17/7059
See application file for complete search history.

(56) References Cited

U.S. PATENT DOCUMENTS

| 3,741,205 A | 6/1973 | Markolf et al. |
| 4,175,555 A | 11/1979 | Herbert |
| 4,484,570 A | 11/1984 | Sutter et al. |
| 5,120,171 A | 6/1992 | Lasner |
| 5,226,766 A | 7/1993 | Lasner |
| 5,360,452 A | 11/1994 | Engelhardt et al. |

(Continued)

*Primary Examiner* — Christian Sevilla
(74) *Attorney, Agent, or Firm* — Phillips Ryther & Winchester; Matthew D. Thayne

(57) ABSTRACT

Medical device locking mechanisms and related methods and systems. In some embodiments, the medical device may comprise an outer surface defining one or more fastener openings configured for receiving one or more fasteners. The one or more fasteners may comprise an upper surface configured to be engaged by a component of the locking system to prevent fastener backout. A plurality of petal structures may be configured to be selectively expanded or contracted to engage the head portion and retain the at least one fastener within the fastener opening to prevent the fastener from backing out of the fastener opening. A biasing member may selectively engage the plurality of petal structures to either expand or contract the plurality of petal structures to facilitate locking the fastener(s) in place within the device.

15 Claims, 13 Drawing Sheets

(56) References Cited

U.S. PATENT DOCUMENTS

| | | |
|---|---|---|
| 5,417,533 A | 5/1995 | Lasner |
| 5,454,365 A | 10/1995 | Bonutti |
| 5,492,442 A | 2/1996 | Lasner |
| 5,562,672 A | 10/1996 | Huebner et al. |
| 5,601,553 A | 2/1997 | Trebing et al. |
| 5,643,269 A | 7/1997 | Harle |
| 5,681,311 A | 10/1997 | Foley et al. |
| 5,871,486 A | 2/1999 | Huebner et al. |
| 5,885,286 A | 3/1999 | Sherman et al. |
| 5,899,906 A | 5/1999 | Schenk |
| 5,947,965 A | 9/1999 | Bryan |
| 5,954,722 A | 9/1999 | Bono |
| 5,964,768 A | 10/1999 | Huebner |
| 5,997,541 A | 12/1999 | Schenk |
| 6,048,344 A | 4/2000 | Schenk |
| 6,117,173 A | 9/2000 | Taddia |
| 6,129,730 A | 10/2000 | Bono et al. |
| 6,224,602 B1 | 5/2001 | Hayes |
| 6,235,033 B1 | 5/2001 | Brace et al. |
| 6,241,731 B1 | 6/2001 | Fiz |
| 6,293,949 B1 | 9/2001 | Justis et al. |
| 6,331,179 B1 | 12/2001 | Freid et al. |
| 6,375,657 B1 | 4/2002 | Doubler et al. |
| 6,602,255 B1 | 8/2003 | Campbell et al. |
| 6,692,503 B2 | 2/2004 | Foley et al. |
| 6,695,846 B2 | 2/2004 | Richelsoph et al. |
| 6,730,091 B1 | 5/2004 | Pfefferle et al. |
| 6,761,719 B2 | 7/2004 | Justis et al. |
| 6,780,186 B2 | 8/2004 | Errico et al. |
| 6,926,098 B2 | 8/2005 | Peter |
| 6,955,677 B2 | 10/2005 | Dahners |
| 7,001,389 B1 | 2/2006 | Navarro et al. |
| 7,175,624 B2 | 2/2007 | Konieczynski et al. |
| 7,195,633 B2 | 3/2007 | Medoff et al. |
| 7,299,630 B2 | 11/2007 | Browne et al. |
| 7,322,983 B2 | 1/2008 | Harris |
| 7,637,928 B2 | 12/2009 | Fernandez |
| 7,691,133 B2 | 4/2010 | Partin et al. |
| 7,749,257 B2 | 7/2010 | Medoff |
| 7,819,905 B2 | 10/2010 | Newcomb et al. |
| 7,887,547 B2 | 2/2011 | Campbell et al. |
| 7,935,137 B2 | 5/2011 | Gorhan et al. |
| 8,496,691 B2 | 7/2013 | Blain |
| 2002/0016595 A1 | 2/2002 | Michelson |
| 2002/0120273 A1 | 8/2002 | Needham et al. |
| 2003/0105462 A1* | 6/2003 | Haider .......... A61B 17/7059 606/86 B |
| 2004/0073218 A1 | 4/2004 | Dahners |
| 2004/0104047 A1 | 6/2004 | Peter |
| 2004/0127899 A1 | 7/2004 | Konieczynski et al. |
| 2004/0220571 A1 | 11/2004 | Assaker et al. |
| 2004/0236333 A1 | 11/2004 | Lin |
| 2005/0096657 A1 | 5/2005 | Autericque et al. |
| 2005/0149027 A1 | 7/2005 | Campbell et al. |
| 2005/0154392 A1 | 7/2005 | Medoff et al. |
| 2005/0165400 A1 | 7/2005 | Fernandez |
| 2005/0210874 A1 | 9/2005 | Browne et al. |
| 2006/0122604 A1 | 6/2006 | Gorhan et al. |
| 2006/0149263 A1 | 7/2006 | Newcomb et al. |
| 2006/0235412 A1 | 10/2006 | Blain |
| 2006/0241612 A1 | 10/2006 | Medoff |
| 2006/0264936 A1 | 11/2006 | Partin et al. |
| 2007/0123884 A1 | 5/2007 | Abdou |
| 2007/0203492 A1 | 8/2007 | Needham et al. |

* cited by examiner

MEDICAL DEVICE LOCKING MECHANISMS AND RELATED METHODS AND SYSTEMS

RELATED APPLICATIONS

This application is a continuation-in-part of co-pending U.S. patent application Ser. No. 11/875,072, filed on Oct. 19, 2007, and titled "CERVICAL PLATE LOCKING MECHANISM AND ASSOCIATED SURGICAL METHOD", which is a continuation-in-part of U.S. patent application Ser. No. 11/804,545, filed on May 18, 2007, and titled "CERVICAL PLATE LOCKING MECHANISM AND ASSOCIATED SURGICAL METHOD." Both of the foregoing applications are hereby incorporated by reference herein in their entireties.

FIELD OF THE INVENTION

Some embodiments disclosed herein relate generally to locking and/or anti-backout mechanisms for various medical devices and/or implants, and related methods. For example, various features and/or components of embodiments disclosed herein may be incorporated into and/or used in conjunction with various implants, including cervical plates, thoracolumbar fixation plates, anterior lumbar fixation plates, standalone interbody devices, bone fracture fixation plates, pedicle screw couplers, such as pedicle screw tulips, and the like.

Some embodiments may comprise one or more novel locking screws and a novel plate that works cooperatively therewith. The locking mechanism, the one or more novel locking screws, and/or a novel plate or other such implants may be used for the fixation/stabilization of the spine, such as the cervical spine. Alternatively, some embodiments may be configured for the fixation/stabilization of the lumbar spine, the sacral spine, and/or the placement of bone grafts, biocompatible inserts, and the like. Still other embodiments may be used for the fixation/stabilization of other anatomical structures and/or non-anatomical structures.

BACKGROUND OF THE INVENTION

The vertebrae of the human spine are generally arranged in a column, with an intervertebral disc disposed between each. These intervertebral discs transmit forces and perform a "cushioning" function. As a result of the stresses and strains continuously applied to the intervertebral discs, as well as disease, degeneration and/or deformity is relatively common. Typically, diseased, degenerated, and/or deformed intervertebral discs are treated by removal and the insertion of an implant, anatomical (i.e., a bone graft) or mechanical (i.e., a biocompatible insert), in the associated intervertebral space. The adjacent vertebrae are preferably immobilized using a plate, such as a cervical plate, during bone graft or biocompatible insert placement and subsequently until they fuse, for example.

Conventional cervical plates typically include a plurality of screw holes and one or more access holes, through which one or more bone grafts or other biocompatible inserts are placed. These cervical plates may span one or multiple levels, with a level defined by the presence of an intervertebral space, and may be secured to the vertebrae of the spine using a plurality of bone screws. Absent some sort of locking mechanism, these bone screws tend to reverse thread, or back out, over time. This reverse threading or backing out is obviously problematic. Various locking mechanisms exist in the art for preventing reverse threading or backing out, and typically involve the use of polymeric bushings, securing caps, securing cover plates, novel thread designs, and the like that prevent the bone screws from disengaging the vertebrae and/or cervical plate subsequent to installation. Many of these locking mechanisms are ineffective, overly complicated, cumbersome to implement, and/or unnecessarily expensive. Thus, what is still needed in the art is a robust, simple, and inexpensive locking mechanism for cervical plates or other medical devices or implants incorporating screws or other fasteners.

SUMMARY

In various exemplary embodiments, the present invention provides such a robust, simple, and inexpensive locking and/or anti-backout mechanism for a screw and/or other fastener of a plate or other medical implant or device. Various embodiments may be elegant in design and effective in performance. Some embodiments may utilize a plate with holes one or more of which may comprise a locking lip structure and/or receiving well, and locking screws that may incorporate a head portion having petal structures that are outwardly biased prior to insertion via an internally-disposed c-ring or another similar biasing member. Advantageously, in some embodiments, the lead-in torque of each of the locking screws is less than the lead-out torque of each of the locking screws. Thus, reverse threading or backing out is prevented.

In a specific example of an embodiment of a fastener locking system for a medical device, such as, for example, a cervical plate, a thoracolumbar fixation plate, an anterior lumbar fixation plate, an intervertebral device, a bone fracture fixation plate, or a pedicle screw coupler, the system may comprise an outer surface defining at least one fastener opening in the outer surface configured for receiving a fastener. The at least one fastener opening may comprise a lip structure positioned adjacent to the outer surface.

The system may further comprise at least one fastener, such as a locking screw, configured to be received in the at least one fastener opening. The at least one fastener may comprise a head portion comprising a plurality of petal structures configured to expand and contract to expand and contract a size of the head portion.

The system may further comprise a biasing member, such as a c-ring, configured to be positioned within the plurality of petal structures to expand a size of the head portion. The at least one fastener may be configured to contract to extend past the lip structure and then be expanded by the biasing member within the head portion such that the petal structures engage the lip structure to inhibit the at least one fastener from being removed from the at least one fastener opening.

In some embodiments, an upper portion of the lip structure may be angled inward towards a central axis of the at least one fastener opening such that the plurality of petal structures contracts as the head portion is inserted into the at least one fastener opening.

In another specific example of an embodiment of a fastener locking system for a medical device, the system may comprise a medical device comprising an outer surface defining at least one fastener opening in the outer surface configured for receiving a fastener. The at least one fastener opening may be defined at least in part by a plurality of petal structures configured to expand and contract.

The system may comprise a biasing member configured to be positioned around the plurality of petal structures to provide an inward bias to the plurality of petal structures and contract a size of the at least one fastener opening.

The system may further comprise at least one fastener configured to be received in the at least one fastener opening. The at least one fastener may comprise a head portion configured to be retained in the at least one fastener opening by the plurality of petal structures and the biasing member.

In some embodiments, the head portion may comprise an upper surface, and the plurality of petal structures may be configured to engage the upper surface after the biasing member has been positioned around the plurality of petal structures with the at least one fastener in the at least one fastener opening.

In some embodiments, the biasing member may be configured to be positioned concentrically around the plurality of petal structures.

In still another specific example of a fastener locking system for a medical device, the system may comprise a medical device comprising an outer surface defining one or more fastener openings configured for receiving a fastener. The system may comprise at least one fastener configured to be received in the at least one fastener opening. The at least one fastener may comprise a head portion comprising an upper surface.

The system may further comprise a plurality of petal structures configured to be selectively expanded or contracted to engage the head portion and retain the at least one fastener within the at least one fastener opening to inhibit the fastener from backing out of the at least one fastener opening. A biasing member may be configured to selectively engage the plurality of petal structures to either expand or contract the plurality of petal structures between an open configuration in which the at least one fastener is able to be removed from the at least one fastener opening and a closed configuration in which the at least one fastener is at least inhibited from being removed from the at least one fastener opening. The plurality of petal structures may be configured to engage the upper surface of the at least one fastener in the closed configuration.

In some embodiments, the plurality of petal structures may be part (in some embodiments an integral part) of the head portion. In some such embodiments, the biasing member may be configured to be positioned within the plurality of petal structures to expand a size of the head portion.

In some embodiments, the plurality of petal structures may together define a central driver bore configured to be engaged by a keyed tool. In some such embodiments, the central driver bore may comprise a polygonal shape.

In some embodiments, at least a subset of the plurality of petal structures may comprise an inner groove configured to receive the biasing member therein. In some such embodiments, each of the plurality of petal structures may comprise an inner groove configured to receive the biasing member therein.

In some embodiments, the plurality of petal structures may at least partially define the at least one fastener opening, and the biasing member may be configured to be positioned around the plurality of petal structures to provide an inward bias to the plurality of petal structures.

In some embodiments, the at least one fastener opening may comprise a lip structure positioned adjacent to the outer surface. As mentioned elsewhere herein, in some such embodiments, the petal structures may be configured to retain the fastener within the fastener opening beneath the lip structure such that the lip structure contacts an upper surface of a head portion of the fastener.

The features, structures, steps, or characteristics disclosed herein in connection with one embodiment may be combined in any suitable manner in one or more alternative embodiments.

BRIEF DESCRIPTION OF THE DRAWINGS

Various embodiments are illustrated and described herein with reference to the various drawings, in which like reference numbers are used to denote like system components and/or method steps, as appropriate, and in which:

FIG. 2 is an exploded perspective view of one exemplary embodiment of the novel locking screw design of FIG. 1, the locking screw including a head portion that incorporates a plurality of petal structures that are outwardly biased by an internally-disposed c-ring or the like;

DETAILED DESCRIPTION OF THE INVENTION

As described above, in various exemplary embodiments, the present invention provides a robust, simple, and inexpensive locking and/or anti-backout mechanism. Some embodiments may be elegant in design and effective in performance, and may utilize a plate with holes that each incorporate a locking lip structure and/or receiving well. Associated locking screws may each incorporate a head portion having petal structures that are outwardly biased prior to insertion via an internally-disposed c-ring or the like. Advantageously, in some embodiments, the lead-in torque of each of the locking screws is less than the lead-out torque of each of the locking screws. Thus, reverse threading or backing out may be prevented.

Figure 1:
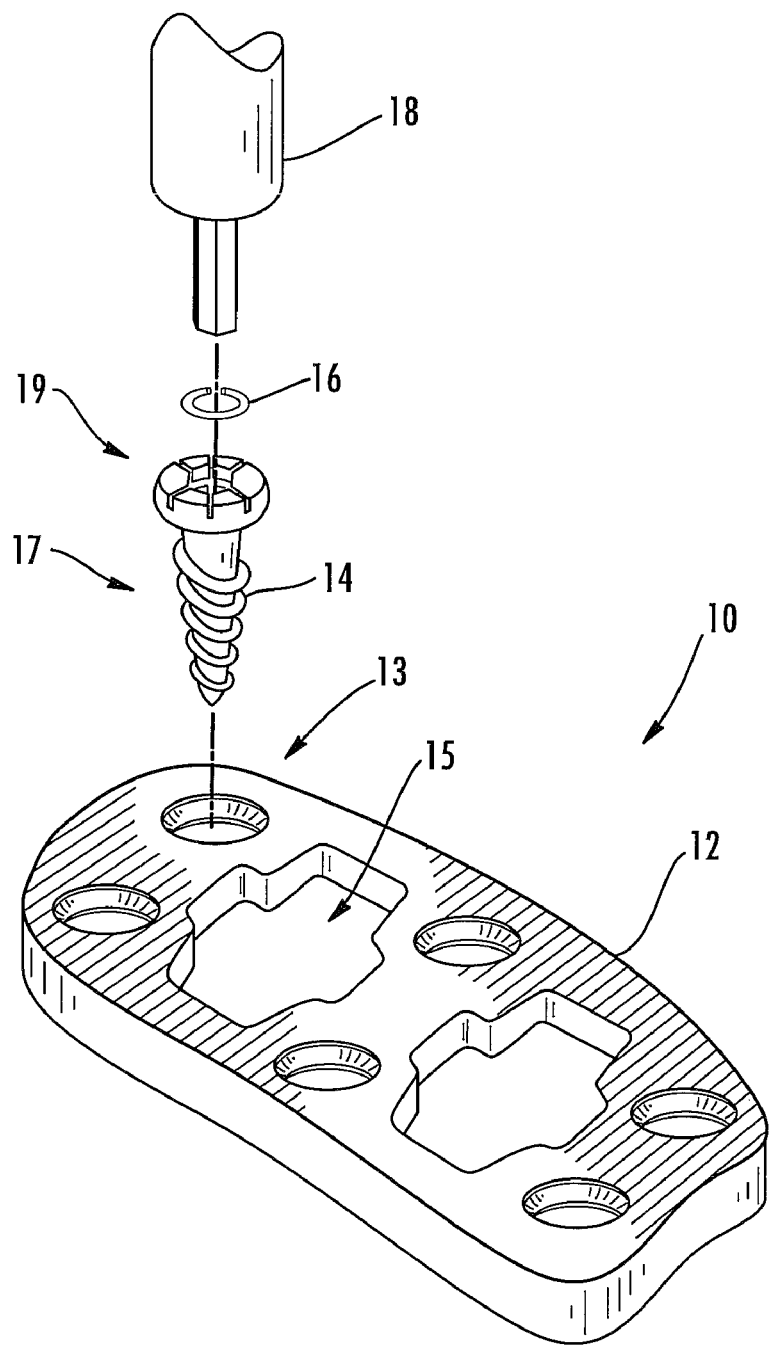
FIG. 1 is an exploded perspective view of one exemplary embodiment of the cervical plate locking mechanism of the present invention (being installed using a keyed screwdriver or the like), the cervical plate locking mechanism including both novel plate and novel locking screw designs.

FIG. 1 is an exploded perspective view of one exemplary embodiment of a cervical plate locking mechanism 10 of the present invention (being installed using a keyed tool, such as a keyed screwdriver 18 or the like), the cervical plate locking mechanism 10 including both novel plate and novel locking screw designs, as are described in greater detail herein below. Specifically, the cervical plate locking mechanism 10 comprises a plate 12 that is configured to be securely fixed to adjacent vertebrae of the cervical spine or the like via one or more locking screws 14 and one or more c-rings 16. The keyed screwdriver 18 may be used to drive the one or more locking screws 14 through the plate 12 and into the adjacent vertebrae.

The plate 12 may comprise one or more screw-receiving holes 13 and, optionally, one or more access holes 15 for the placement of one or more bone grafts, biocompatible inserts, or the like. Preferably, the plate 12 is manufactured from a biocompatible material and is sized such that it achieves its intended purpose. Material, shape, and size selection may be selected according to the knowledge of those of ordinary skill in the art. Each of the one or more locking screws 14 may comprise a threaded portion 17 and a head portion 19. The threaded portion 17 of each of the one or more locking screws 14 may be configured to pass through the one or more screw-receiving holes 13 of the plate 12 and securely fix the plate 12 to the adjacent vertebrae. Thread selection is well known to those of ordinary skill in the art.

The head portion 19 of each of the one or more locking screws 14 may be configured to securely engage each of the one or more locking screws 14 with the plate 12. As described in greater detail herein below, the head portion 19 of each of the one or more locking screws 14 may be outwardly biased by the c-ring 16, or by another similar biasing member or other mechanism or feature. Such mechanism or feature may be inserted and/or compressed into the head portion 19 of a given locking screw 14. In some embodiments, the head portion 19 may expand automatically upon insertion of the c-ring 16.

The c-ring 16, or another comparable mechanism, and the head portion 19 of the given locking screw 14 may be again compressed and subsequently allowed to expand as they are inserted into a given screw-receiving hole 13 of the plate 12. More specifically, in some embodiments, the head portion 19 of a given locking screw 14 may be allowed to expand in the receiving well of the given screw-receiving hole 13. This insertion may be accomplished using, for example, a matching flat, triangle, square, star, hexagon, octagon, or other keyed screwdriver 18, as appropriate. Preferably, the shape of the outside of the head portion 19 of each of the locking screws 14 substantially corresponds to the shape of the inside of the associated receiving well, although this is not a requirement.

Figure 2:
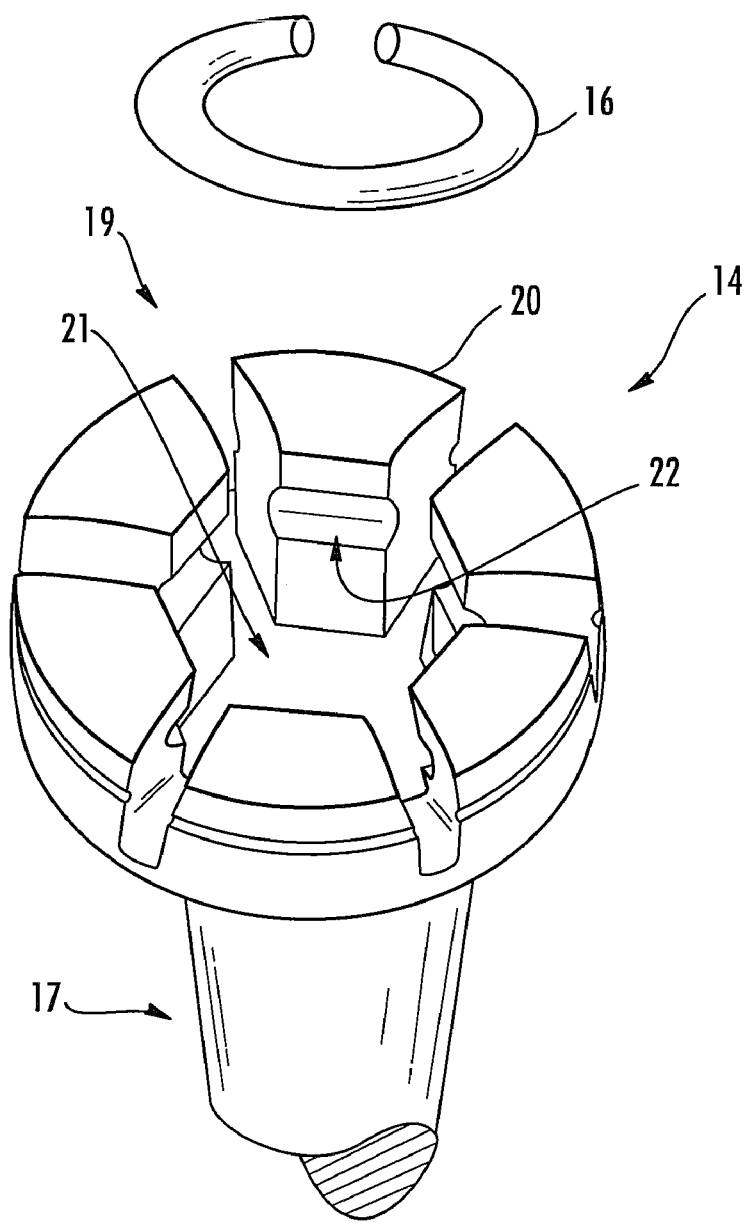

FIG. 2 is an exploded perspective view of one exemplary embodiment of the novel locking screw design of FIG. 1, the locking screw 14 including a head portion 19 that incorporates a plurality of petal structures 20 that are outwardly biased by the internally-disposed c-ring 16 or the like. Locking screw 14 and/or its accompanying locking features may be incorporated into and/or used in conjunction with various implants, such as cervical plates, thoracolumbar fixation plates, anterior lumbar fixation plates, standalone interbody devices, bone fracture fixation plates, pedicle screw couplers, such as pedicle screw tulips, and the like.

As described above, c-ring 16, or other comparable mechanism, may be selectively inserted and/or compressed into the head portion 19 of a given locking screw 14, and then allowed to expand. The c-ring 16, or other comparable mechanism, and the head portion 19 of the given locking screw 14 may then be compressed again and subsequently allowed to expand as they are inserted into a given screw-receiving hole 13 (FIG. 1) of plate 12 (FIG. 1), or of another screw-receiving hole of another plate or other implant or medical device.

More specifically, the head portion 19 of the given locking screw 14 may be allowed to expand in a receiving well of the given screw-receiving hole 13. This insertion may be accomplished using a matching flat, triangle, square, star, hexagon, octagon, or other keyed screwdriver 18 (as shown in FIG. 1), as appropriate.

Preferably, the shape of the outside of the head portion 19 of each of the locking screws 14 at least substantially corresponds to the shape of the inside of the associated receiving well, although this is not a requirement. Accordingly, the head portion 19 of each of the locking screws 14 may comprise a plurality of concentrically-arranged petal structures 20 that are disposed around a central driver bore 21, which may have a shape corresponding to that of the keyed screwdriver 18. In one exemplary embodiment, the plurality of petal structures 20 may be formed by cutting concentrically-arranged slots into the head portion 19 of the locking screw 14. Thus, the plurality of petal structures 20 may, in some embodiments and implementations, be integrally formed with the head portion 19 of the locking screw 14. Alternatively, the plurality of petal structures 20 may be formed separately and then joined to the head portion 19 of the locking screw 14.

The material characteristics and/or configuration of the plurality of petal structures 20 may, in some embodiments, impart the plurality of petal structures 20 with an inherent outward bias, which bias in some embodiments may be independent of the c-ring 16 or other comparable mechanism, although this is not required.

Figure 3:
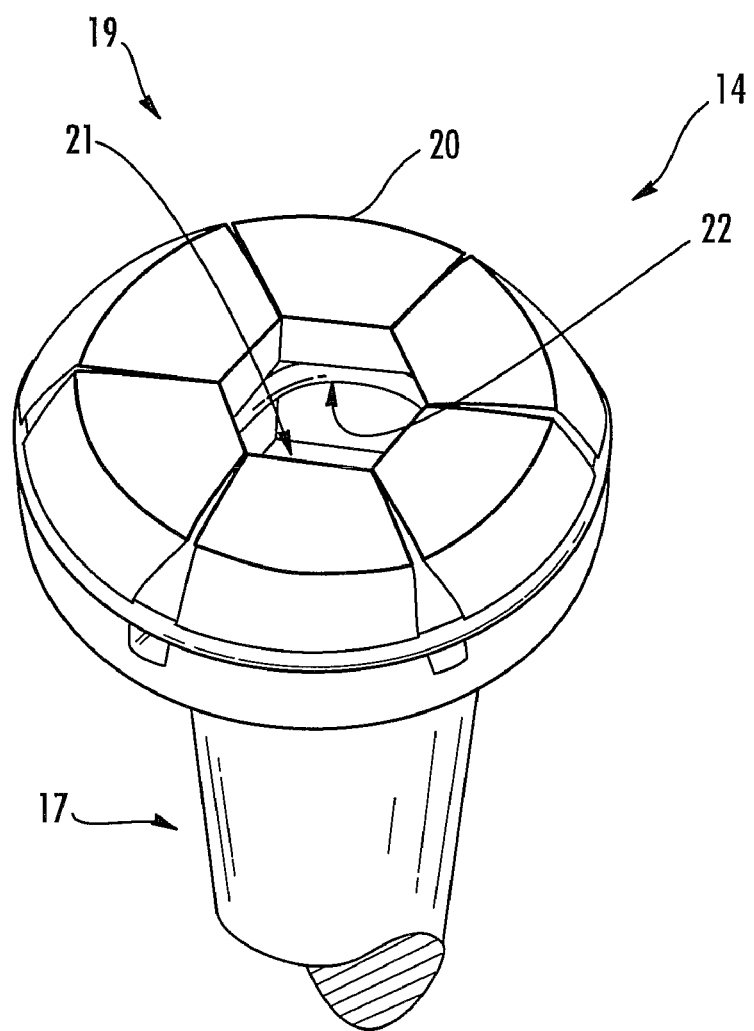
FIG. 3 is a perspective view of the novel locking screw design of FIGS. 1 and 2, the locking screw being in its "as inserted" state, with the c-ring being installed and the head portion being compressed.

In some embodiments, the plurality of petal structures 20 may define an inner groove 22 extending around an inner perimeter of head portion 19, such as around an exterior perimeter of central driver bore 21, as shown in FIG. 2. Inner groove 22 may be configured to receive and retain the c-ring 16 or other comparable mechanism within the head portion 19 of the locking screw 14. FIG. 2 illustrates the head portion 19 of the locking screw 14 in an "unlocked" configuration, with the plurality of petal structures 20 being "open," either due to the eventual insertion of the c-ring 16 or other comparable mechanism, or inherently. FIG. 3 illustrates the head portion 19 of the locking screw 14 in a "locked" configuration, with the plurality of petal structures 20 being "closed," either inherently or due to the eventual insertion of the head portion 19 of the locking screw 14 into a receiving well. Thus, in some embodiments, the plurality of petal structures 20 may be configured to be flexibly biased towards a locked/closed configuration such that the petals 20 can be flexed open to an unlocked/open configuration to receive c-ring 16 and then automatically revert to a locked/closed configuration with c-ring 16 therein. In some embodiments, the presence of c-ring 16 within head portion 19 may partially flex petals 20 towards an unlocked/open configuration (but not fully) so as to enlarge the diameter of head portion 19 and retain head portion 19 within a locking hole of a device, such as cervical plate 12.

It can also be seen in FIGS. 2 and 3 that petal structures 20 each partially defines an upper surface of head portion 19 of locking screw 14. In the depicted embodiment, this upper surface is flat. In this manner, the upper surface of head portion 19 may be engaged with a lip structure of a locking hole of a device, such as cervical plate 12, as discussed in greater detail below. FIGS. 2 and 3 further depict that petal structures 20 together define central driver bore 21 (as shown in FIG. 3) comprising a polygonal opening, and can be expanded by flexing petal structures 20 (as shown in FIG. 2) such that petal structures 20 no longer define the same bore opening. In this manner, a keyed tool, such as keyed screwdriver 18, may be used to expand central driver bore 21 by inserting the keyed tool and rotating it. This may allow for the c-ring 16 to be inserted into inner groove 22. FIG. 3 also illustrates that, in a closed configuration, petal structures 20 at least substantially enclose c-ring 16 within head portion 19 to prevent inadvertent removal of c-ring 16 after a locking screw 14 has been fully engaged within a corresponding receiving hole 13.

Figure 4:
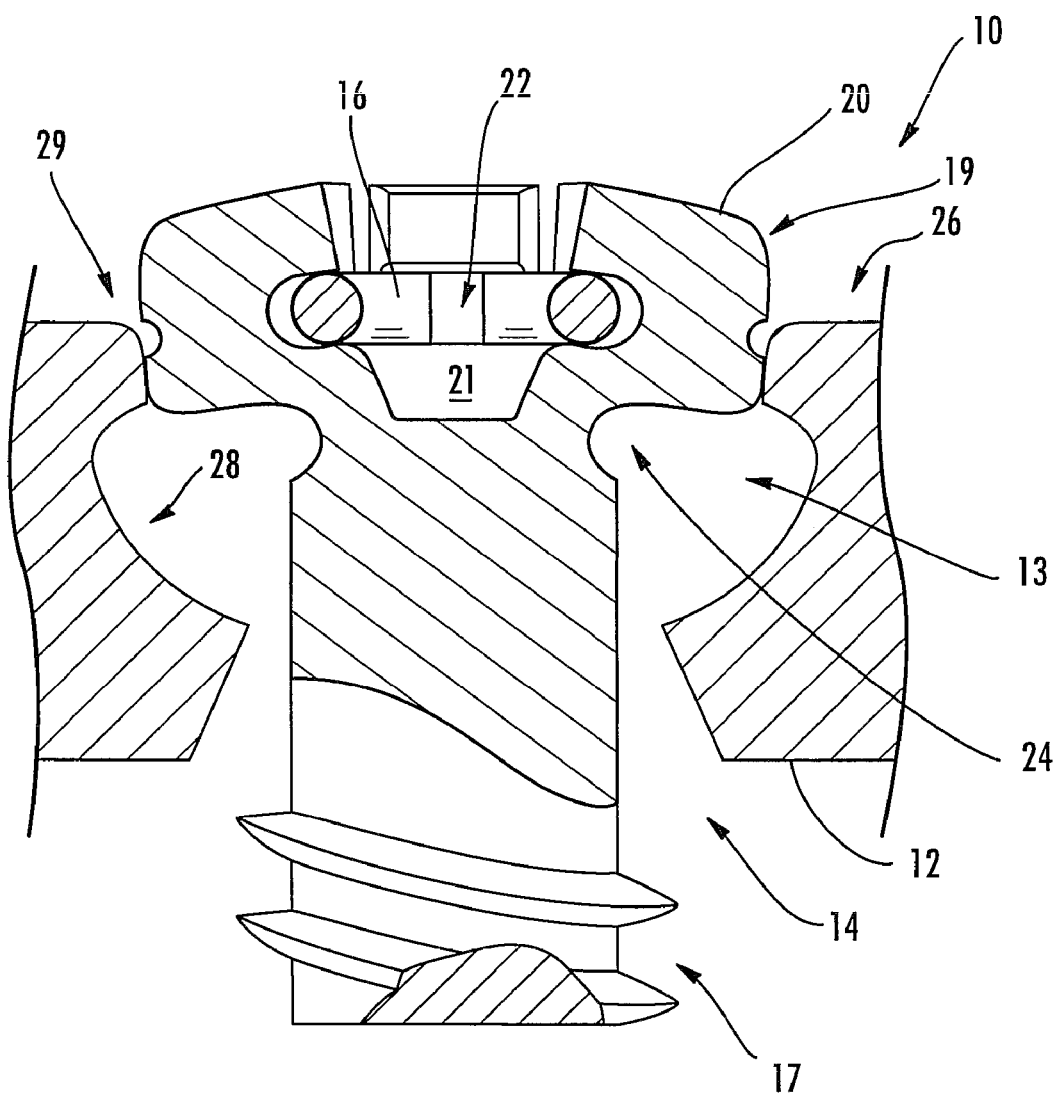
FIG. 4 is a partial cross-sectional view of the cervical plate locking mechanism of FIG. 1, the novel locking screw of FIGS. 1-3 in the process of being inserted into the novel plate of FIG. 1.

FIG. 4 is a partial cross-sectional view of the cervical plate locking mechanism 10 of FIG. 1, the novel locking screw 14 of FIGS. 1-3 in the process of being inserted into the novel plate 12 of FIG. 1. It should be noted that the head portion 19 of the locking screw 14, and specifically the lower, outer portion of each of the plurality of petal structures 20, optionally incorporates a recessed or otherwise weakened area 24, or flexure, in order to facilitate the flexibility and/or outward biasing of the plurality of petal structures 20 by the c-ring 16 or other comparable mechanism, after it is inserted into the inner groove 22 that is manufactured into the middle, inner portion of each of the plurality of petal structures 20.

One or more of the one or more screw-receiving holes 13 of the plate 12 or other such device may comprise an annular lip structure 26 through which the head portions 19 of the locking screws 14 may be inserted (with a compression/expansion action). This annular lip structure 26 may serve to retain the head portion 19 of the given locking screw 14 once it is fully inserted and expanded, thereby preventing the reverse threading or backing out of the locking screw 14.

Figure 5:
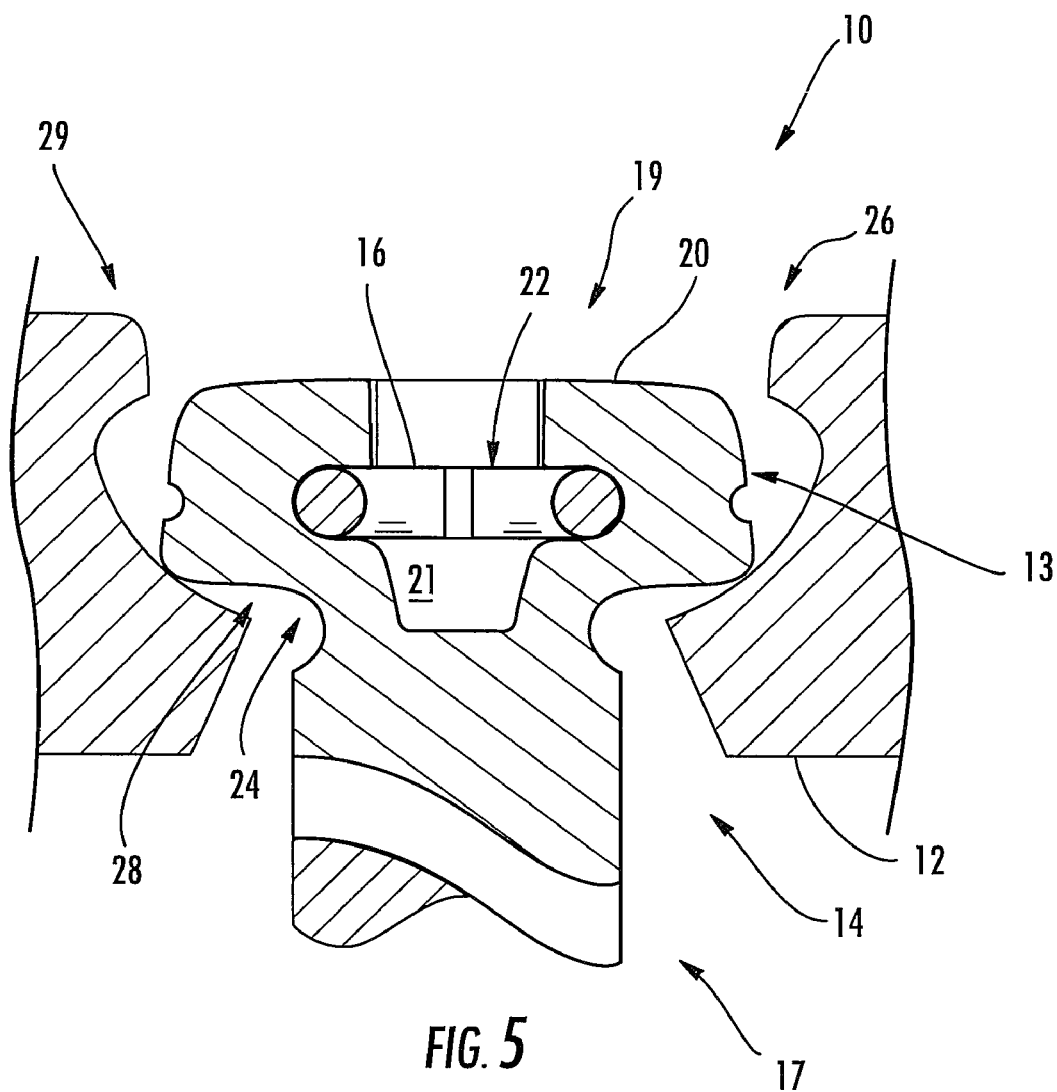
FIG. 5 is a partial cross-sectional view of the cervical plate locking mechanism and locking screw of FIGS. 1-4 being fully inserted into the novel plate of FIGS. 1 and 4.
Figure 6:
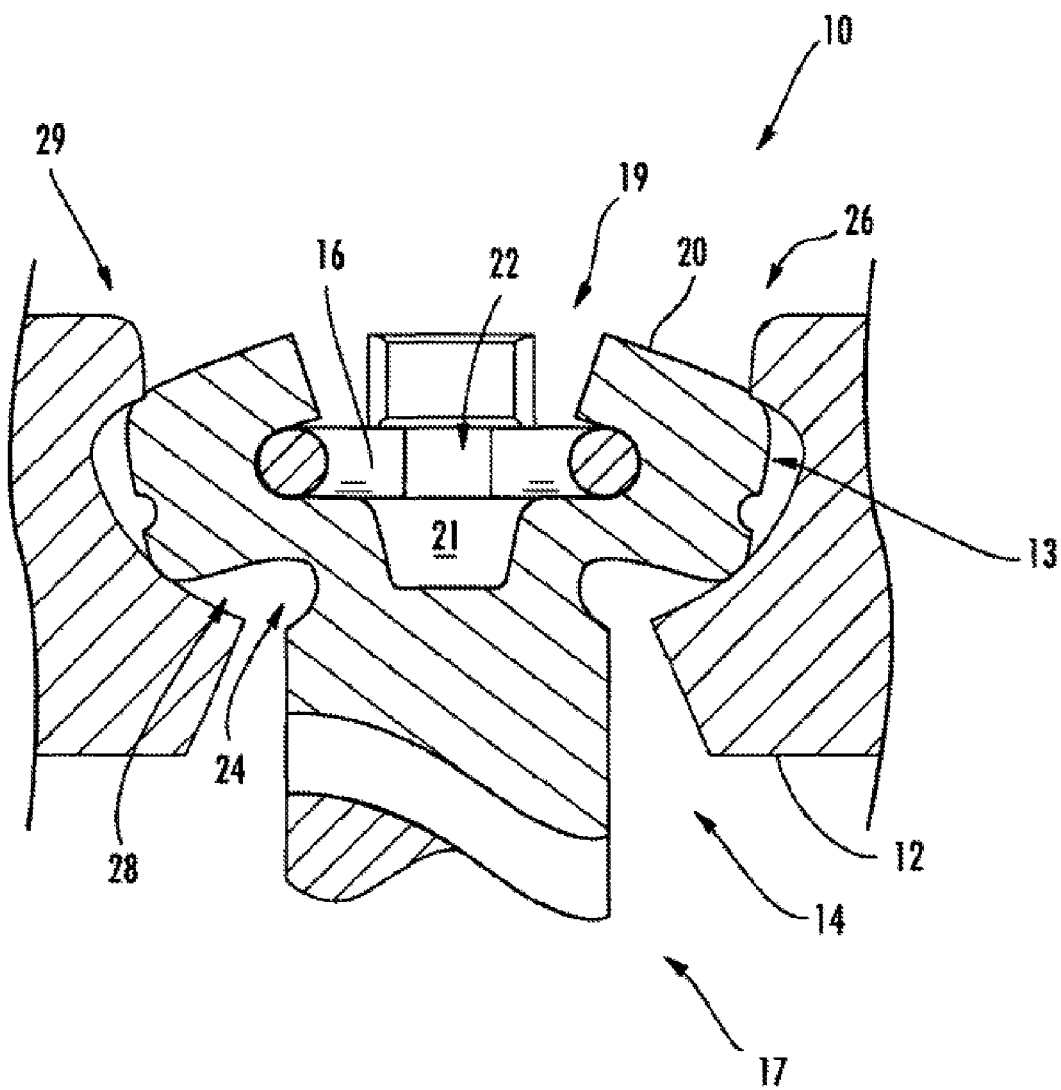
FIG. 6 is a partial cross-sectional view of the cervical plate locking mechanism and locking screw of FIGS. 1-5 after the locking screw has been fully inserted into the locking plate and allowed to expand therein.

Optionally, the inner annular surface 28 of each of the screw-receiving holes 13 of the plate 12 may be curved in a generally concave manner, as shown in FIGS. 4-6, but shaped such that the lead-in torque of a given locking screw 14 is less than the lead-out torque or the locking screw 14, i.e., the inner annular surface angles adjacent to the outer surface 29 of the plate 12 (at the "top" and "bottom" of the lip structure 26) vary as experienced by an inserted locking screw 14 versus a removed locking screw 14, with the "top" angle being greater (more vertical or steep) and the "bottom" angle being smaller (more horizontal or shallow), for example.

As also shown in FIGS. 4-6, the portion of the lip structure 26 immediately adjacent to the upper surface of petal structures 20 is preferably angled slightly inward towards a center axis of central driver bore 21 to facilitate desirable feel and function of head portion 19 of the locking screw 14 fitting into screw-receiving hole 13 and preventing backout of locking screw 14 thereafter.

FIG. 5 is a partial cross-sectional view of the cervical plate locking mechanism 10 of FIGS. 1 and 4, the novel locking screw 14 of FIGS. 1-4 being fully inserted into the novel plate 12 of FIGS. 1 and 4. Again, it should be noted that the head portion 19 of the locking screw 14, and specifically the lower, outer portion of each of the plurality of petal structures 20, optionally incorporates a recessed or otherwise weakened area 24, or flexure, in order to facilitate the flexibility and/or outward biasing of the plurality of petal structures 20 by the c-ring 16 or other comparable mechanism, after it is inserted into the inner groove 22 that is manufactured into the middle, inner portion of each of the plurality of petal structures 20. Each of the one or more screw-receiving holes 13 of the plate 12 may comprise an annular lip structure 26 through which the head portions 19 of the locking screws 14 are inserted (with a compression-expansion action).

This annular lip structure 26 serves to retain the head portion 19 of the given locking screw 14 once it is fully inserted and expanded, as illustrated, thereby preventing the reverse threading or backing out of the locking screw 14. As described above, optionally, the inner annular surface 28 of each of the screw-receiving holes 13 of the plate 12 is curved in a generally concave manner, but shaped such that the lead-in torque of a given locking screw 14 is less than the lead-out torque or the locking screw 14, i.e. the inner annular surface angles adjacent to the outer surface 29 of the plate 12 (at the "top" and "bottom" of the lip structure 26) vary as experienced by an inserted locking screw 14 versus a removed locking screw 14, with the "top" angle being greater (more vertical or steep) and the "bottom" angle being smaller (more horizontal or shallow), for example.

FIG. 6 depicts head portion 19 of locking screw 14 after it has been allowed to expand within receiving hole 13 by the expansion of c-ring 16. As depicted in this figure, once this expansion takes place, an upper surface of head portion 19 of locking screw 14 contacts a lower surface of lip structure 26 to retain locking screw 14 in place and prevent, or at least reduce the possibility of, backup.

Thus, some embodiments may be configured to have a first, fully open configuration in which the petal structures 20 are fully open to receive c-ring 16, a second, partially open configuration in which c-ring 16 flexes petal structures 20 partially open, and a third, fully-closed configuration in which c-ring 16 is absent and petal structures 20 are able to fully compress together.

Figure 7:
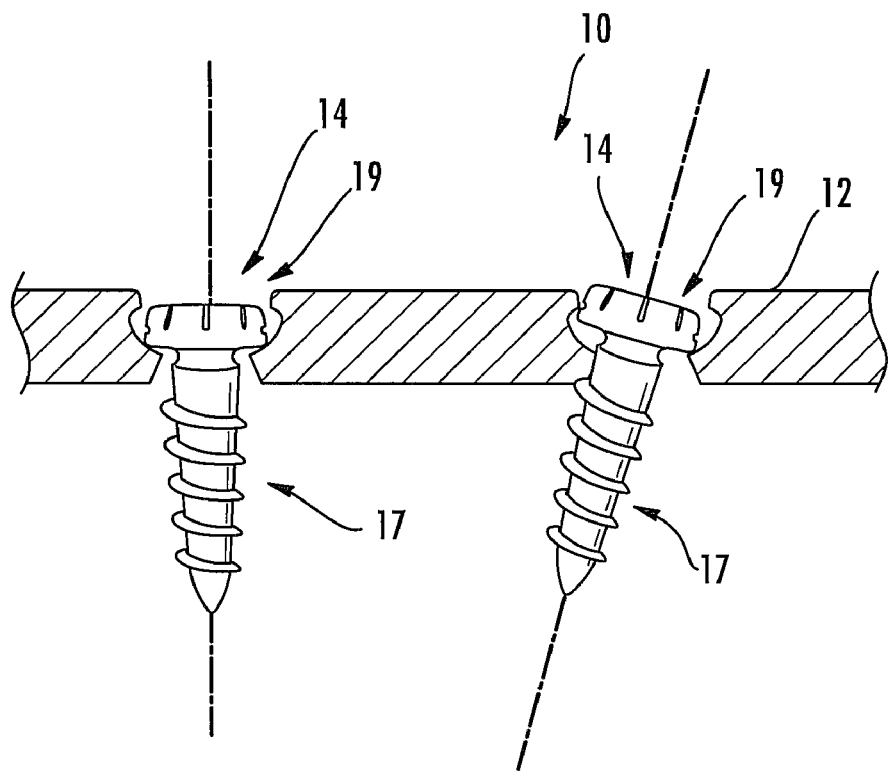
FIG. 7 is a partial cross-sectional view of the cervical plate locking mechanism of FIGS. 1, 4, and 5, the novel locking screws of FIGS. 1-5 being inserted into the novel plate of FIGS. 1, 4, and 5 at various exemplary angles.
Figure 8:
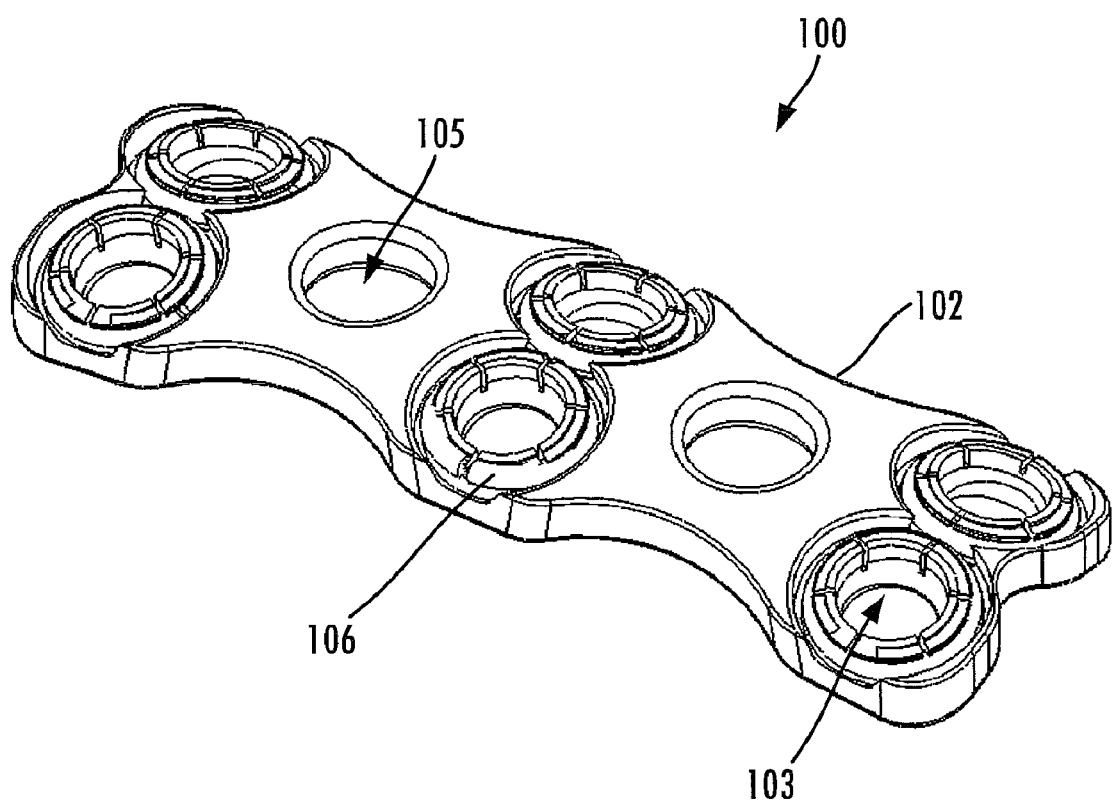
FIG. 8 is a perspective view of another exemplary embodiment of the cervical plate locking mechanism of the present invention, the cervical plate locking mechanism again including both novel locking plate and novel screw (not illustrated) designs.
Figure 9:
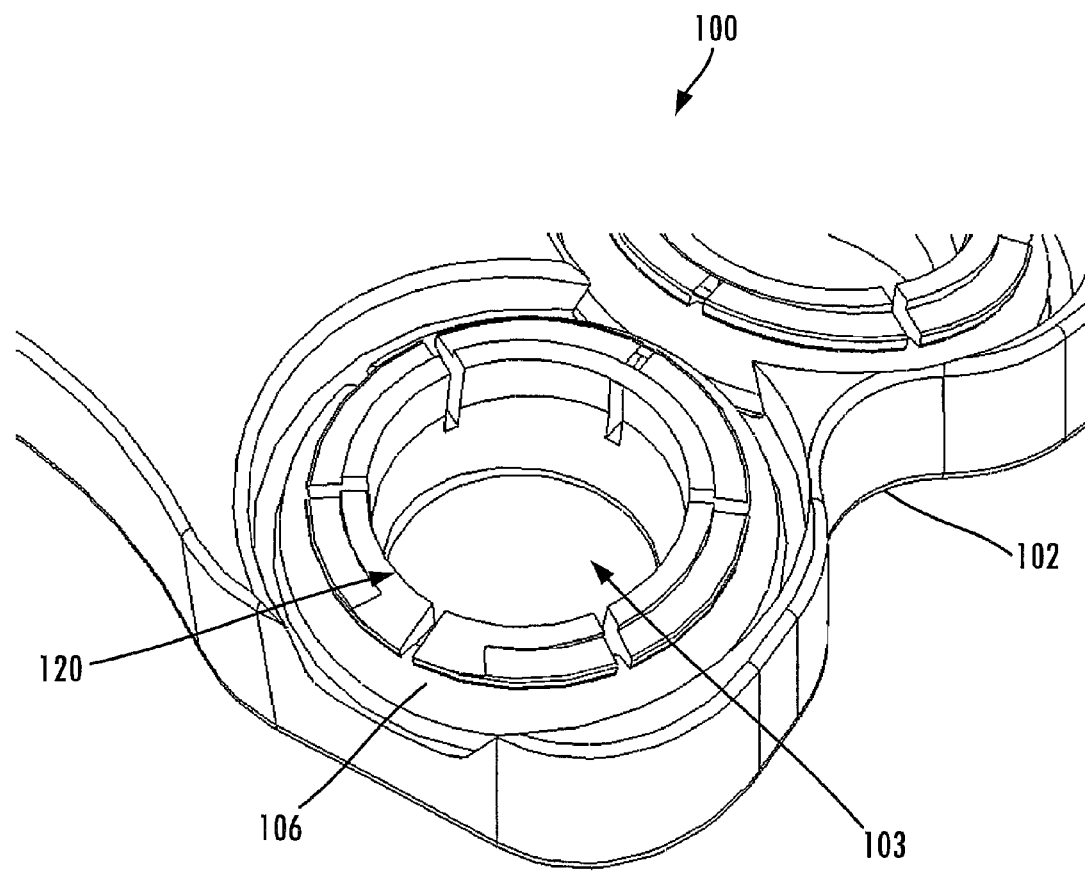
FIG. 9 is a partial perspective view of the cervical plate locking mechanism of FIG. 7, the novel locking plate incorporating one or more screw-receiving holes each including a plurality of petal structures configured to engage and retain the novel screws (not illustrated)
Figure 10:
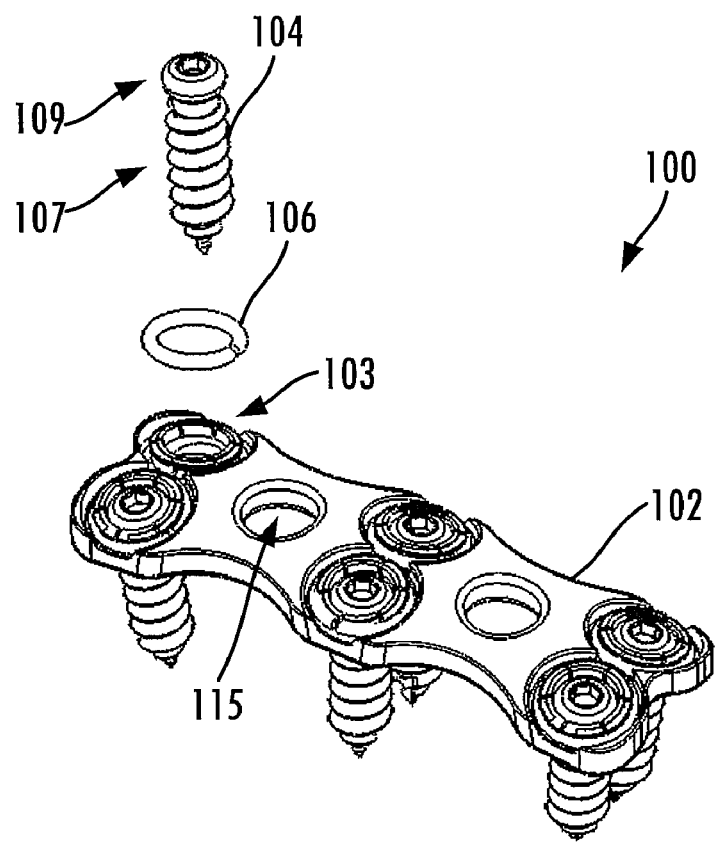
FIG. 10 is an exploded perspective view of the cervical plate locking mechanism of FIGS. 7 and 8, a novel screw being inserted into a screw-receiving hole of the novel locking plate.
Figure 11:
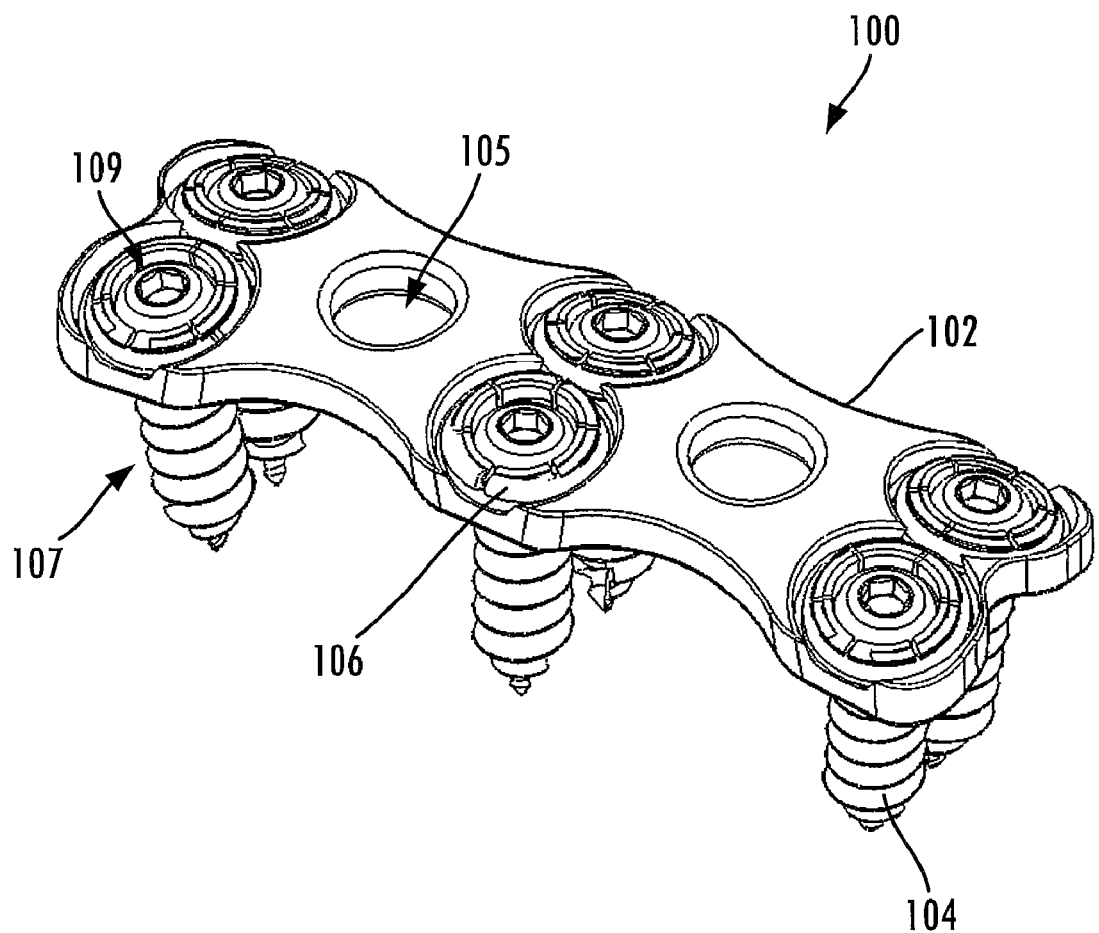
FIG. 11 is a perspective view of the cervical plate locking mechanism of FIGS. 7-9, novel screws fully inserted into all of the screw-receiving holes of the novel locking plate.
Figure 12:
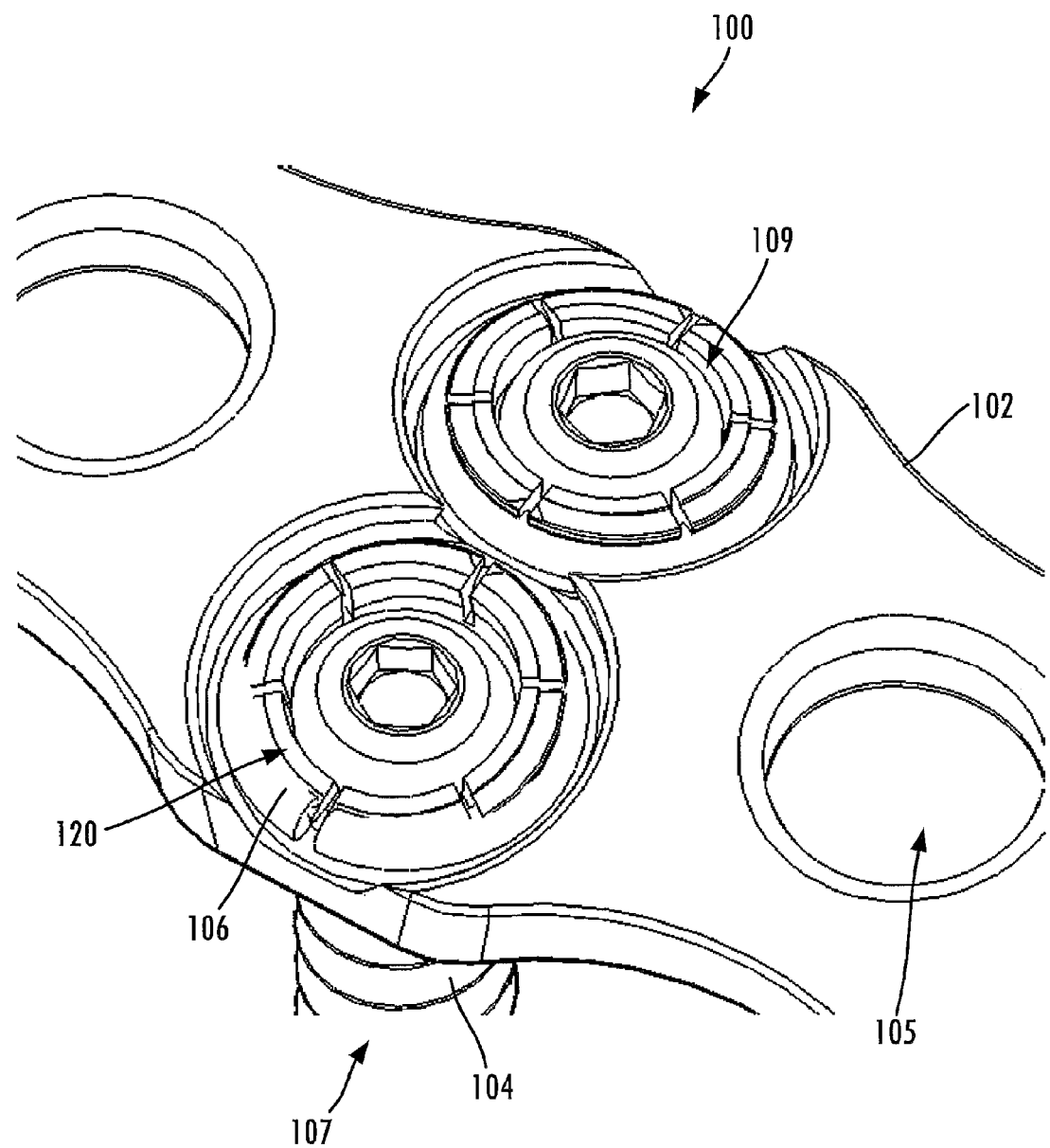
FIG. 12 is a partial perspective view of the cervical plate locking mechanism of FIGS. 7-10, novel screws fully inserted into all of the screw-receiving holes of the novel locking plate.

FIG. 7 is a partial cross-sectional view of the cervical plate locking mechanism 10 of FIGS. 1, 4, 5, and 6 the novel locking screws 14 of FIGS. 1-5 being inserted into the novel plate 12 of FIGS. 1, 4, 5, and 6 at various exemplary angles relative to both the plate 12 and the underlying vertebrae. In this embodiment, each of the receiving wells may be asymmetrical in shape such that the head portion 19 of each of the locking screws 14 snugly and securely engages the receiving well, although this is not necessarily illustrated. In other words, each of the receiving wells may be appropriately angled in the plate 12 in order to receive each of the angled locking screws 14.

Referring to FIGS. 8-13, in another exemplary embodiment of a locking mechanism 100 of the present invention, the locking mechanism 100 again comprises both novel locking plate and novel screw designs, as are described in greater detail herein below. Locking mechanism 100 also comprises a cervical plate locking mechanism although, as mentioned above, this locking mechanism may be applied to a wide variety of other devices and implants, such as thoracolumbar fixation plates, anterior lumbar fixation plates, standalone interbody devices, bone fracture fixation plates, pedicle screw couplers, such as pedicle screw tulips, and the like.

More specifically, the cervical plate locking mechanism 100 comprises a locking plate 102 that is configured to be securely fixed to adjacent vertebrae of the cervical spine or the like via one or more screws 104 and one or more c-rings 106. The keyed screwdriver (not illustrated) is used to drive the one or more screws 104 through the locking plate 102 and into the adjacent vertebrae. The locking plate 102 comprises one or more screw-receiving holes 103 and, optionally, one or more access holes 105 for the placement of one or more bone grafts, biocompatible inserts, or the like.

In some embodiments, the locking plate 102 may be manufactured from a biocompatible material and may be sized such that it achieves its intended purpose. Material, shape, and size selection may be selected by those of ordinary skill in the art. Each of the one or more screws 104 may comprise a threaded portion 107 and a head portion 109. The threaded portion 107 of each of the one or more screws 104 may be configured to pass through the one or more screw-receiving holes 103 of the locking plate 102 and securely fix the locking plate 102 to the adjacent vertebrae. Thread selection may be as desired to those of ordinary skill in the art.

The head portion 109 of each of the one or more screws 104 is configured to securely engage each of the one or more screws 104 with the locking plate 102. As described in greater detail herein below, a plurality of petal structures 120 disposed about each of the screw-receiving holes 103 may be inwardly biased by the c-ring 106. Petal structures 120 may be incorporated into plate 102, or into another implant or device comprising screw-receiving holes. A c-ring 106, or another comparable mechanism may be expanded and subsequently allowed to contract around the petal structures 120 as the head portion 109 of a screw 104 is disposed in the receiving well of the given screw-receiving hole 103. This insertion may be accomplished using a matching flat, triangle, square, star, hexagon, octagon, or other keyed screwdriver, as appropriate. Preferably, the shape of the outside of the head portion 109 of each of the screws 104 substantially corresponds to the shape of the inside of the associated receiving well, although this is not a requirement. Thus, in this exemplary embodiment, the plurality of petal structures 120 and the c-ring 106 have been shifted from the one or more screws 104 to the locking plate 102, accomplishing the same purposes.

Figure 13:
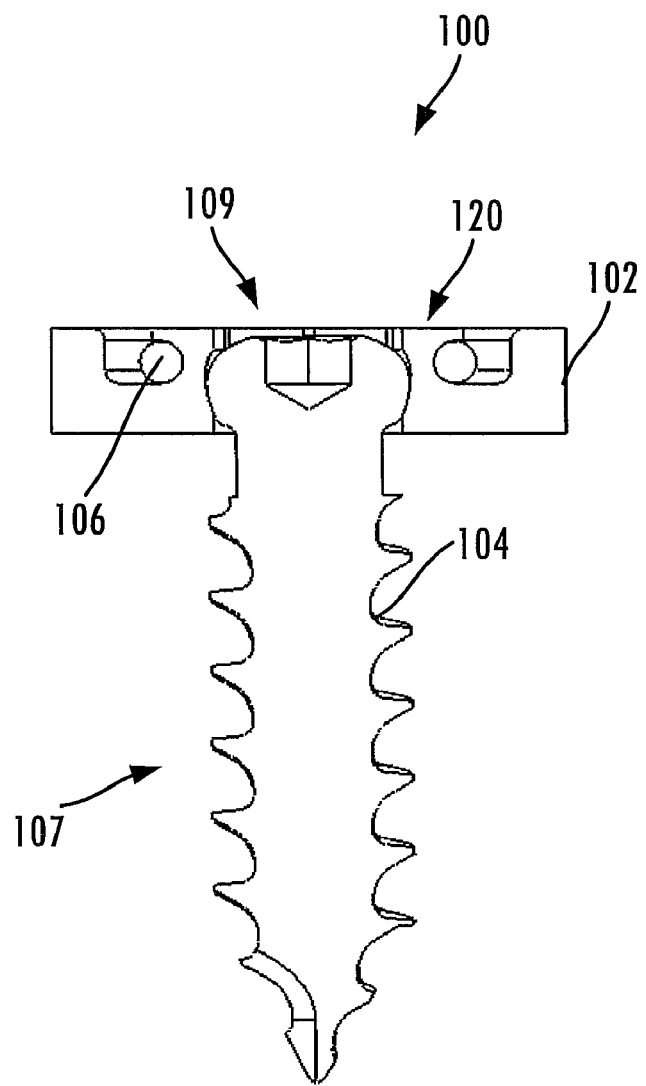
FIG. 13 is a partial cross-sectional view of the cervical plate locking mechanism of FIGS. 7-11, a novel screws fully inserted into a screw-receiving holes of the novel locking plate.

It can be best seen in FIG. 13 that, once screw 104 is positioned in the receiving well/hole 103 and c-ring 106 has been positioned about the plurality of petal structures 120, at least a portion of the locking mechanism (namely, a portion of the petal structures 120) extends above a top surface of screw 104 to secure screw 104 within hole 103 and prevent, or at least inhibit, backout of screw 104.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

The invention claimed is:

1. A fastener locking system for a medical device, comprising:
   a medical device comprising an outer surface, wherein the medical device defines at least one fastener opening in the outer surface configured for receiving a fastener, and wherein the at least one fastener opening comprises a lip structure positioned adjacent to the outer surface;
   at least one fastener configured to be received in the at least one fastener opening, wherein the at least one fastener comprises a head portion comprising a plurality of petal structures configured to expand and contract to expand and contract a size of the head portion; and
   a biasing member configured to be positioned within the plurality of petal structures to expand a size of the head portion, wherein the at least one fastener is configured to contract to extend past the lip structure and then be expanded by the biasing member within the head portion such that the petal structures engage the lip structure to inhibit the at least one fastener from being removed from the at least one fastener opening.

2. The fastener locking system of claim 1, wherein the medical device comprises one of a cervical plate, a thoracolumbar fixation plate, an anterior lumbar fixation plate, an intervertebral device, a bone fracture fixation plate, and a pedicle screw coupler.

3. The fastener locking system of claim 1, wherein the biasing member comprises a c-ring.

4. The fastener locking system of claim 1, wherein the at least one fastener comprises at least one locking screw.

5. The fastener locking system of claim 1, wherein the at least one fastener comprises a threaded portion.

6. The fastener locking system of claim 5, wherein the threaded portion is configured to engage with a bony structure of a patient.

7. The fastener locking system of claim 1, wherein an upper portion of the lip structure is angled inward towards a central axis of the at least one fastener opening such that the plurality of petal structures contracts as the head portion is inserted into the at least one fastener opening.

8. A fastener locking system for a medical device, comprising:
   a medical device comprising an outer surface, wherein the device defines at least one fastener opening in the outer surface configured for receiving a fastener;
   at least one fastener configured to be received in the at least one fastener opening, wherein the at least one fastener comprises a head portion comprising an upper surface;
   a plurality of petal structures configured to be selectively expanded or contracted, wherein the plurality of petal structures is configured to be either selectively expanded or contracted to engage the head portion and retain the at least one fastener within the at least one fastener opening to inhibit the fastener from backing out of the at least one fastener opening; and
   a biasing member configured to selectively engage the plurality of petal structures to either expand or contract the plurality of petal structures between an open configuration in which the at least one fastener is able to be removed from the at least one fastener opening and a closed configuration in which the at least one fastener is at least inhibited from being removed from the at least one fastener opening, and wherein the plurality of petal structures are configured to engage the upper surface of the at least one fastener in the closed configuration.

9. The fastener locking system of claim 8, wherein the plurality of petal structures are part of the head portion, and wherein the biasing member is configured to be positioned within the plurality of petal structures to expand a size of the head portion.

10. The fastener locking system of claim 9, wherein the plurality of petal structures together define a central driver bore configured to be engaged by a keyed tool.

11. The fastener locking system of claim 10, wherein the central driver bore comprises a polygonal shape.

12. The fastener locking system of claim 9, wherein at least a subset of the plurality of petal structures comprises an inner groove configured to receive the biasing member therein.

13. The fastener locking system of claim 10, wherein each of the plurality of petal structures comprises an inner groove configured to receive the biasing member therein.

14. The fastener locking system of claim 8, wherein the at least one fastener opening comprises a lip structure positioned adjacent to the outer surface.

15. The fastener locking system of claim 8, wherein the biasing member comprises a c-ring.

* * * * *